US007827991B2

(12) United States Patent
Maher (10) Patent No.: US 7,827,991 B2
(45) Date of Patent: Nov. 9, 2010

(54) METHOD AND SYSTEM FOR PREVENTING HEAD INJURY

(75) Inventor: Gerald J. Maher, South Weymouth, MA (US)

(73) Assignee: Mahercor Laboratories, LLC, South Weymouth, MA (US)

( * ) Notice: Subject to any disclaimer, the term of this patent is extended or adjusted under 35 U.S.C. 154(b) by 756 days.

(21) Appl. No.: 11/181,589

(22) Filed: Jul. 14, 2005

(65) Prior Publication Data

US 2006/0011204 A1 Jan. 19, 2006

Related U.S. Application Data

(60) Provisional application No. 60/588,271, filed on Jul. 15, 2004.

(51) Int. Cl.
*A61F 11/00* (2006.01)
*A61F 5/56* (2006.01)
*A61C 5/14* (2006.01)
*A61C 3/00* (2006.01)

(52) U.S. Cl. .................. 128/857; 128/848; 128/859; 128/861; 128/862; 433/6

(58) Field of Classification Search ............ 128/848, 128/857, 859–862; 433/5–6, 215, 223
See application file for complete search history.

(56) References Cited

U.S. PATENT DOCUMENTS

| 4,457,708 | A | * | 7/1984 | Dufour | 433/6 |
| 4,727,867 | A | * | 3/1988 | Knoderer | 128/859 |
| 5,052,409 | A | | 10/1991 | Tepper | 128/859 |
| 5,092,346 | A | | 3/1992 | Hays et al. | 128/848 |
| 5,194,003 | A | * | 3/1993 | Garay et al. | 433/215 |
| 5,299,936 | A | * | 4/1994 | Ueno | 433/71 |
| 5,368,447 | A | * | 11/1994 | Schwendemann et al. | 417/54 |
| 5,462,066 | A | | 10/1995 | Snyder | 128/848 |
| 5,511,562 | A | | 4/1996 | Hancock | 128/859 |
| 5,692,523 | A | | 12/1997 | Croll et al. | 128/859 |
| 5,826,581 | A | * | 10/1998 | Yoshida | 128/859 |
| 5,924,422 | A | * | 7/1999 | Gustafson | 128/846 |
| 5,931,164 | A | | 8/1999 | Kiely et al. | 128/859 |
| 6,092,524 | A | | 7/2000 | Barnes, Sr. | 128/859 |

(Continued)

OTHER PUBLICATIONS

Elliot J. Pellman, "Background on the National Football League's Research on Concussion in Professional Football," *Neurosurgery*, vol. 53, No. 4, Oct. 2003, pp. 797-798.

(Continued)

*Primary Examiner*—Patricia M Bianco
*Assistant Examiner*—Brandon Jackson
(74) *Attorney, Agent, or Firm*—Greenberg Traurig, LLP; David J. Dykeman; Danielle T. Abramson (57) ABSTRACT

A method and system for preventing head injury by providing parallel alignment of a jaw are disclosed. A method of preventing a head injury comprises providing a dental appliance having a left body, a right body and a lingual bar engaging the left body and the right body; placing the dental appliance over a plurality of teeth of a lower jaw so the lower jaw and a upper jaw are approximately parallel; and absorbing a force applied to the lower jaw, wherein the dental appliance absorbs the force applied to the lower jaw while preventing a condyle of a mandible from transferring the force to a temporal bone.

20 Claims, 8 Drawing Sheets

U.S. PATENT DOCUMENTS

| | | | |
|---|---|---|---|
| 6,371,758 B1 | 4/2002 | Kittelsen | 433/6 |
| 6,588,430 B2 | 7/2003 | Kittelsen et al. | 128/859 |
| 6,626,180 B1 * | 9/2003 | Kittelsen et al. | 128/859 |
| 6,691,710 B2 | 2/2004 | Kittelsen et al. | 128/859 |
| 2003/0205234 A1 | 11/2003 | Bardach et al. | 128/861 |
| 2004/0038183 A1 * | 2/2004 | Jacobs et al. | 433/215 |

OTHER PUBLICATIONS

International Search Report based on PCT/US05/25030 dated Jan. 25, 2007.

* cited by examiner

METHOD AND SYSTEM FOR PREVENTING HEAD INJURY

RELATED APPLICATIONS

This application which claims the benefit of U.S. Provisional Application No. 60/588,271 filed on Jul. 15, 2004, the entirety of which is incorporated herein by reference.

FIELD

The presently disclosed embodiments relate to preventing head injury, and more specifically to a method and system for preventing head injury by providing parallel alignment of a jaw.

BACKGROUND

Mild head injuries, such as concussions, account for approximately 600,000 hospital admissions per year. Mild traumatic brain injury ("MTBI") is a traumatically induced alteration in brain function that is manifested by an alteration of awareness or consciousness, including but not limited to loss of consciousness, "ding," sensation of being dazed or stunned, sensation of "wooziness" or "fogginess," seizure, or amnesic period; and signs and symptoms commonly associated with postconcussion syndrome.

A concussion is an alteration of consciousness, disturbance in vision and equilibrium caused by a direct blow to the head, rapid acceleration and/or deceleration of the head, or direct blow to the base of the skull from a vertical impact to the chin. The most common cause of a concussion is a blow to the head, with people participating in high impact contact sports especially at risk. Concussions result in complications including severe headaches, dizziness, earaches, facial pain, ringing in the ears, nausea, irritability, confusion, disorientation, dizziness, amnesia, concentration difficulty, blurred vision, sleep disturbance, increased size of one pupil, severe weakness in an arm or leg, photophobia, vertigo, impaired speech and permanent brain damage.

The brain is a soft, jell-like structure covered with a dense network of blood vessels and contains billions of nerve cells and a complexity of interconnecting fibers. The brain is a well-protected part of the body enclosed in a strong bony case, referred to as the skull, and cushioned in a bath of water, called the cerebrospinal fluid. A blow to the head causes the brain to rebound against the skull, potentially causing a tearing and twisting of the structures and blood vessels of the brain resulting in a disturbance of function of the electrical activity of the nerve cells in the brain and a breakdown of the usual flow of messages within the brain. The blow to the head can cause multiple shearing injuries which stretch and tear the soft nerve tissue and cause multiple points of bleeding from small blood vessels of the brain. A blow to the jaw causes the jaw bone to violently come into contact with an adjacent area of the skull, causing jarring and damage. Athletes, in particular, suffer frequent blows to the jaw with the highest frequency for athletes participating in contact sports. Approximately 95% of concussions suffered while playing football are the result of the lower jaw relaying the shock of impact to the brain. As many as approximately 40% of retired National Football League (NFL) players may suffer from permanent brain damage from the result of multiple concussions. In addition, over 90% of brain concussions resulting in unconsciousness to athletes come from a blow or trauma to the jaw.

Dental injuries account for the most common type of orofacial injury during athletic activities. Orofacial injuries are injuries to the jaw and teeth. Every athlete involved in contact sports has about a 10% chance per season of suffering an orofacial injury, or about a 33% to about a 56% chance during an athletic career. Though a majority of dental injuries can be prevented by using a mouthguard, the extent of prevention of dental injuries lies in the ability of a mouthguard to better align the jaw of an athlete. Mouthguards are flexible devices worn in athletic and recreation activities to protect the teeth and mouth from trauma.

U.S. Pat. No. 6,588,430 to Kittelson et al. discloses a composite performance enhancing mouthguard with embedded wedge. The Kittelson et al. mouthguard is composed of multiple distinct materials and is adapted to fit the upper teeth of the mouth of an athlete.

U.S. Pat. No. 6,092,524 to Barnes Sr. discloses a mouthguard designed to minimize discomfort and speech interference associated with conventional mouthpieces. The Barnes Sr. mouthguard includes a pair of posterior portions molded to receive and overlay the posterior teeth where the posterior portions are interconnected with a front portion that overlays the incisors. The front portion of the Barnes Sr. mouthguard is dimensioned to cover substantially all of the front surface of the incisors while leaving the lower or cutting edge of the incisors exposed.

U.S. Pat. No. 5,931,164 to Kiely et al. discloses an athletic mouthguard including a U-shaped base portion, an upwardly projecting inner flange portion joined to an inner edge of the base portion and an upwardly projecting outer flange portion joined to an outer edge of the base portion. The Kiely et al. mouthguard is molded from a composition including a light pervious foundation material and a light reflective aggregate distributed throughout the foundation material.

Previous mouthguards do not effectively prevent head injury in athletes. Prior art mouthguards do not adapt to the differing mouth structures of athletes, and do not effectively provide a shock absorbing mechanism from blows to the jaw. Prior art mouthguards inadequately compensate for unparallel jaw alignment to effectively prevent transfer of force to the brain. Therefore, there remains a need in the art for a safe, comfortable and effective dental appliance that provides parallel alignment of the jaw while absorbing the force from a blow to the jaw.

SUMMARY

The presently disclosed embodiments relate to a method and system for preventing head injury by providing parallel alignment of a jaw.

According to aspects illustrated herein, there is provided a method of preventing a head injury comprising: providing a dental appliance having a left body, a right body and a lingual bar engaging the left body and the right body; placing the dental appliance over a plurality of teeth of a lower jaw so the lower jaw and a upper jaw are approximately parallel; and absorbing a force applied to the lower jaw, wherein the dental appliance absorbs the force applied to the lower jaw while preventing a condyle of a mandible from transferring the force to a temporal bone.

According to aspects illustrated herein, there is provided a method of preventing a concussion comprising: providing a dental appliance having a left body, a right body and a lingual bar engaging the left body and the right body; and placing the dental appliance over a portion of a lower set of teeth; wherein the dental appliance positions a maxilla and a mandible in an approximately parallel position to absorb a force applied to a jaw.

According to aspects illustrated herein, there is provided a method of manufacturing a dental appliance to prevent head injury comprising: making a model of the teeth of the upper jaw and the lower jaw; forming a left body to fit over a plurality of teeth of the left lower jaw; forming a right body to fit over a plurality of teeth of the right lower jaw; and engaging a lingual bar to the left body and the right body, the lingual bar having a shape following a contour of the teeth of the lower jaw, wherein the dental appliance covers a plurality of teeth of the lower jaw to place a mandible and a maxilla in an approximately parallel alignment.

According to aspects illustrated herein, there is provided a dental appliance for preventing head injury comprising: a left body; a right body; and a lingual bar spanning from the left body to the right body to engage the left body to the right body, wherein the dental appliance covers a portion of a lower set of teeth while placing a mandible and a maxilla in an approximately parallel alignment.

According to aspects illustrated herein, there is provided a dental appliance for preventing a concussion comprising: a left body; a right body; and a lingual bar engaging the left body and the right body, the lingual bar having a shape following a contour of a lower set of teeth, wherein the dental appliance covers at least a portion of a lower set of teeth to absorb a force applied to a jaw while preventing a condyle of a mandible from transferring the force to a temporal bone.

BRIEF DESCRIPTION OF DRAWINGS

The presently disclosed embodiments will be further explained with reference to the attached drawings, wherein like structures are referred to by like numerals throughout the several views. The drawings are not necessarily to scale, the emphasis having instead been generally placed upon illustrating the principles of the presently disclosed embodiments.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Figure 1:
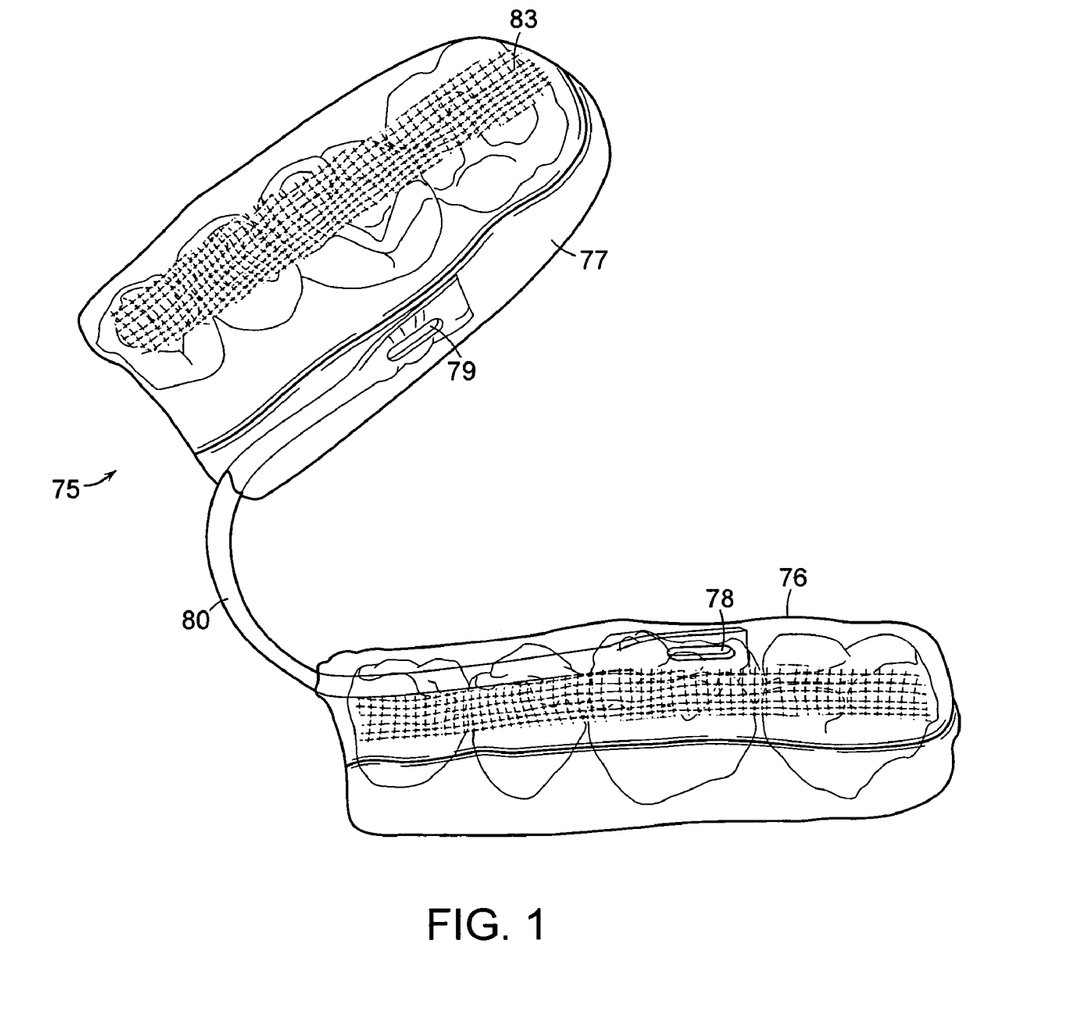
FIG. 1 is a top view of a dental appliance for preventing head injury.
Figure 2:
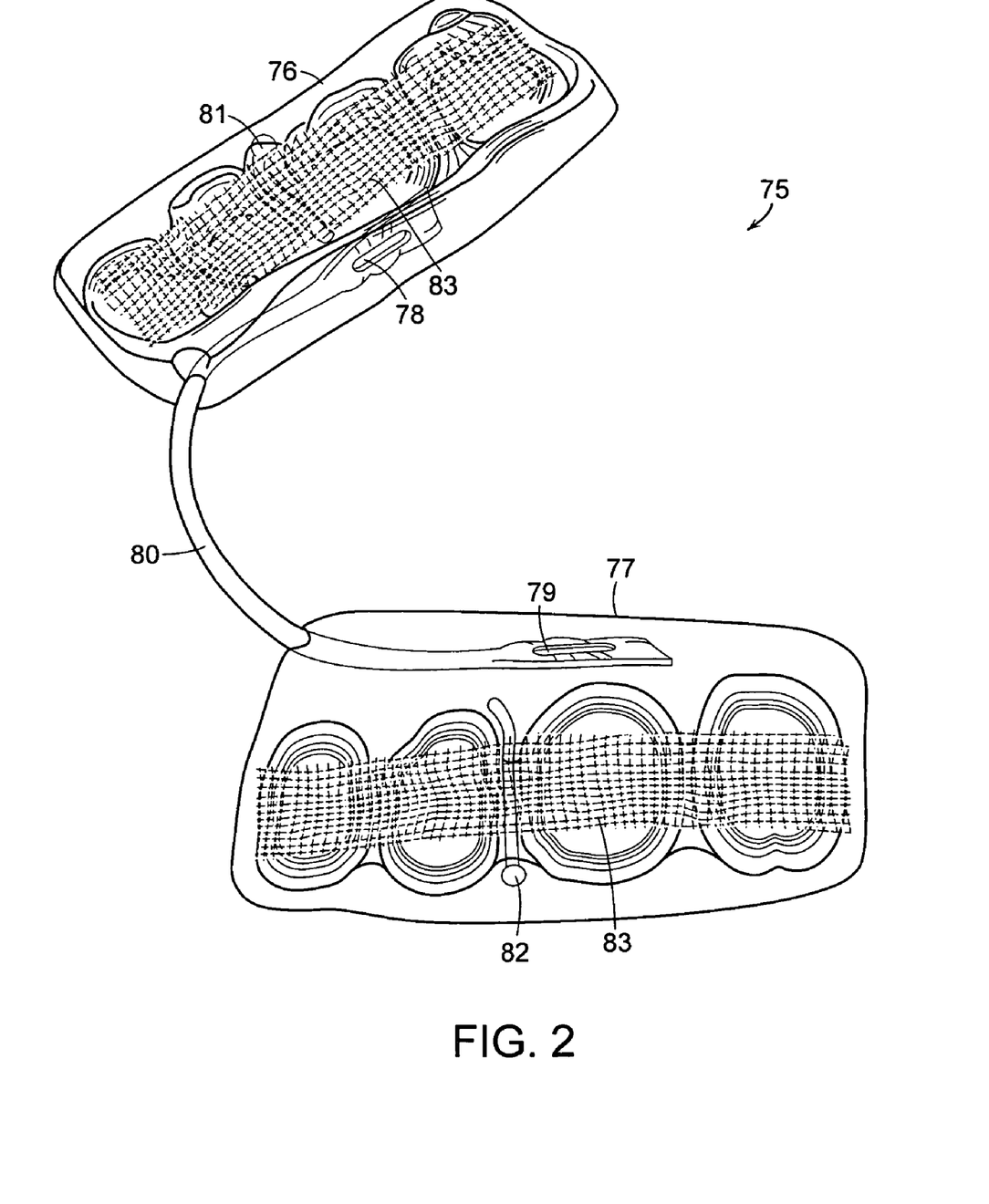
FIG. 2 is a bottom view of a dental appliance for preventing head injury.

The presently disclosed embodiments relate to a method and system for preventing head injury by providing parallel alignment of a jaw. FIG. 1 shows a top view of a dental appliance 75 for preventing head injury. FIG. 2 shows a bottom view of the dental appliance 75 for preventing head injury. The dental appliance 75 comprises a left body 76, a right body 77 and a lingual bar 80 that spans from the left body 76 to the right body 77, engaging the left body 76 to the right body 77. The lingual bar 80 is shaped to follow the contour of the lower set of teeth. A portion of the ends of the lingual bar 80 are embedded within the material comprising the left body 76 and the right body 77. The lingual bar 80 has an opening 78 on the end of the lingual bar 80 on the left body 76 and an opening 79 on the end of the lingual bar 80 on the right body 77. A left ball clasp 81 on the left body 76 and a right ball clasp 82 on the right body 77 extend across a portion of the left body 76 and the right body 77, respectively, for slight retention in the left body 76 and the right body 77 on the teeth of the lower jaw.

The lingual bar 80 comprises a rigid material that resists bending when a force is applied. In an embodiment, the lingual bar 80 comprises stainless steel. In an embodiment, the lingual bar 80 is comprised of materials including, but not limited to, gold, palladium and cobalt chrome. Those skilled in the art will recognize the lingual bar can be comprised of many materials known in the art and be within the spirit and scope of the presently disclosed embodiments.

The left ball clasp 81 and the right ball clasp 82 are approximately L-shaped. At least a portion of the left ball clasp 81 is embedded within the material comprising the left body 76 and at least a portion of the right ball clasp 82 is embedded within the material comprising the right body 77. Those skilled in the art will recognize the left ball clasp and the right ball clasp can be shaped in various configurations and be within the spirit and scope of the presently disclosed embodiments.

The left ball clasp 81 and the right ball clasp 82 comprise stainless steel. In an embodiment, the left ball clasp 81 and the right ball clasp 82 are comprised of a material including, but not limited to, gold, palladium and cobalt chrome. Those skilled in the art will recognize the left ball clasp and the right ball clasp can be comprised of many materials known in the art and be within the spirit and scope of the presently disclosed embodiments.

In an embodiment, the dental appliance 75 comprises a mesh material 83 embedded within the left body 76 and the right body 77 to strengthen the dental appliance 75. The mesh material 83 strengthens the dental appliance 75 by reinforcing the material comprising the left body 76 and the right body 77. The mesh material 83 reduces the tendency for the dental appliance 75 to crack from patients biting down on the dental appliance 75 with excessive force. In an embodiment, the mesh material 83 comprises stainless steel. Those skilled in the art will recognize the mesh material can comprise many materials known in the art and be within the spirit and scope of the presently disclosed embodiments.

The left body 76 and the right body 77 are composed of a material that provides strength to withstand the force of a bite and is moldable to conform to the shape of the teeth. In an embodiment, the left body 76 and the right body 77 are comprised of an acrylic. An acrylic is a thermoplastic comprising a resin having a polymeric structure. Those skilled in the art will recognize the left body and the right body can be comprised of many materials known in the art and be within the spirit and scope of the presently disclosed embodiments. The presently disclosed embodiments can include the mesh material 83 in the acrylic, include other strengthening mechanisms known in the art in the acrylic, or can be composed of acrylic only.

Figure 3:
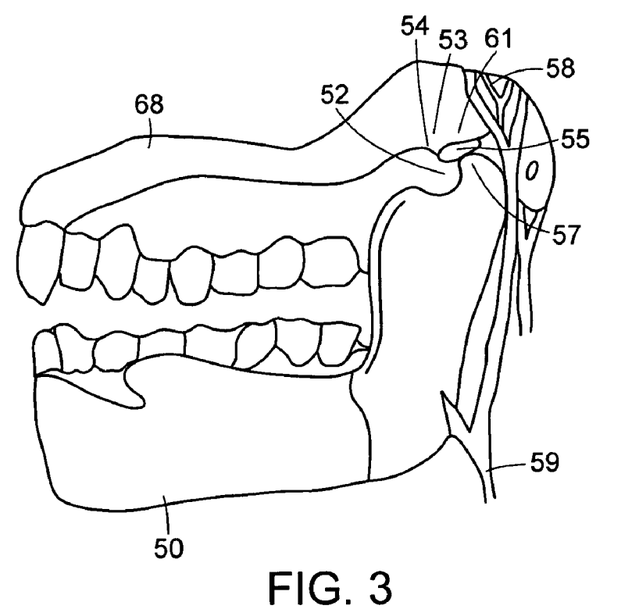
FIG. 3 is a side view of a jaw and a temporomandibular joint.

FIG. 3 shows a side view of a jaw and temporomandibular joint of a user of the protection device of the presently disclosed embodiments. An upper jaw 68, known as a maxilla 68, and a lower jaw 50, known as a mandible 50, are movably connected at a temporomandibular joint (TMJ) 52. A temporal bone 53 is located above and rearward of the mandible 50 and an articular eminence 54 forms the beginning of the socket of the TMJ 52, with a cartilage 55 located rearward and posteriorly to the articular eminence 54. A condyle 57 of the mandible 50 forms the ball of the TMJ 52. A glenoid fossa 61 is a deep concavity in the temporal bone 53 that receives the condyle 57 of the mandible 50. An auriculotemporal nerve 58, a nerve that influences sensory and motor activities of the body, and a supra-temporo artery 59, an artery that provides blood circulation to the head, pass through the TMJ 52.

A blow to the mandible 50 creates wear on the condyle 57 and the cartilage 55. The wear on the condyle 57 and the cartilage 55 causes bone deterioration on the head of the condyle 57 or slippage and compressive damage on the cartilage 55. Impingement of the condyle 57 on the auriculotemporal nerve 58 or the supra-temporo artery 59 can cause loss of consciousness, reduced physical abilities and ultimately a concussion.

The alignment of the jaw affects the impact of a blow to the jaw. For a jaw that is set to an approximately parallel configuration, the impact of a blow to the jaw is less likely to cause the maxilla and mandible to contact one another with as much force as a jaw that is set in a non-parallel position, such as a jaw that is sloped. A sloped jaw is a less stable jaw configuration that increases the susceptibility of suffering a concussion from a blow to the jaw. The articular disc should be positioned superior to the condyle and separate the condyle from the temporal lobe of the brain.

Figure 4:
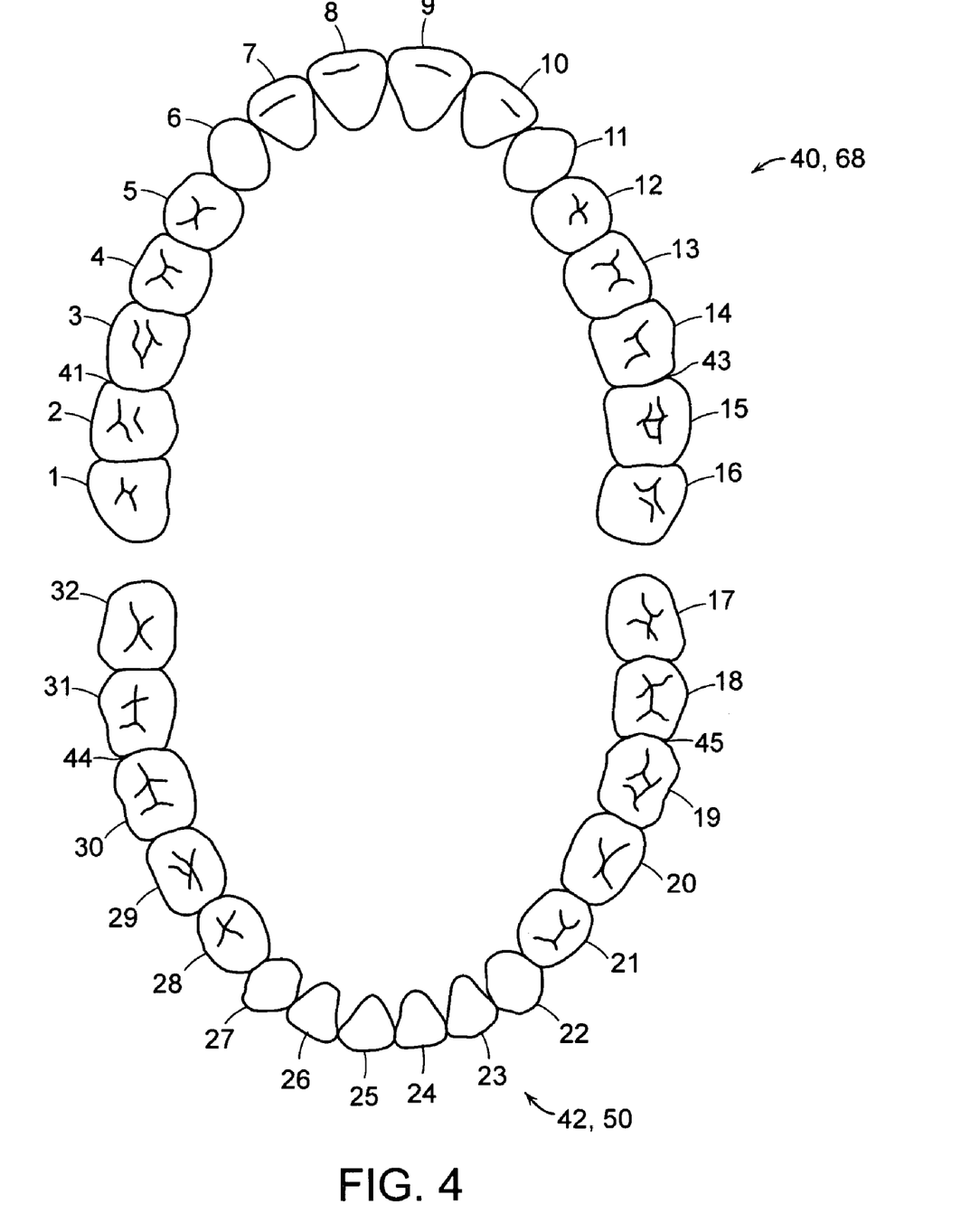
FIG. 4 is a view of an upper set of teeth of a maxilla and a lower set of teeth of a mandible.

FIG. 4 shows a view of an upper set of teeth 40 of the maxilla 68 and a lower set of teeth 42 of the mandible 50. FIG. 4 is an embodiment of a teeth structure. The teeth structure of various individuals can differ from the embodiment shown in FIG. 4. Both the upper set of teeth 40 and the lower set of teeth 42 comprise molars, bicuspids, cuspids, and incisors. More particular, the upper set of teeth 40 in a right side 41 of the maxilla 68 comprises a third molar 1, a second molar 2, a first molar 3, a second bicuspid 4, a first bicuspid 5, a cuspid 6, a lateral incisor 7 and a central incisor 8. Continuing from the central incisor 8 on a left side 43 of the maxilla 68 are a central incisor 9, a lateral incisor 10, a cuspid 11, a first bicuspid 12, a second bicuspid 13, a first molar 14, a second molar 15 and a third molar 16. The lower set of teeth 42 in a left side 45 of the mandible 50 comprise a third molar 17, a second molar 18, a first molar 19, a second bicuspid 20, a first bicuspid 21, a cuspid 22, a lateral incisor 23 and a central incisor 24. Continuing from the central incisor 24 on a right side 44 of the mandible 50 are a central incisor 25, a lateral incisor 26, a cuspid 27, a first bicuspid 28, a second bicuspid 29, a first molar 30, a second molar 31 and a third molar 32.

Figure 5:
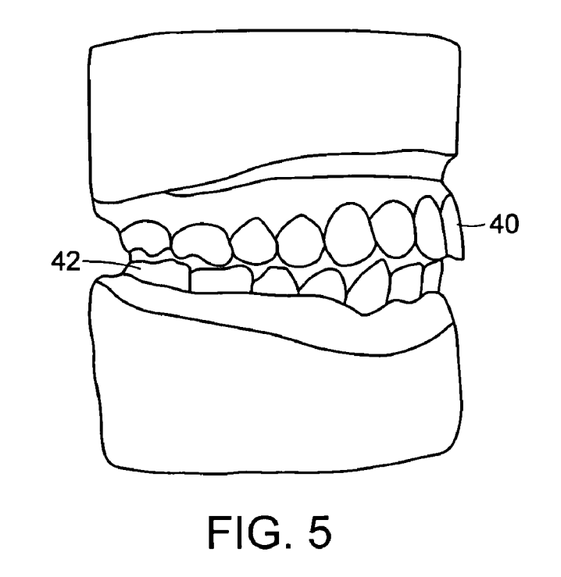
FIG. 5 is a side view of an upper set of teeth and a lower set of teeth during a representative bite of a patient.
Figure 6:
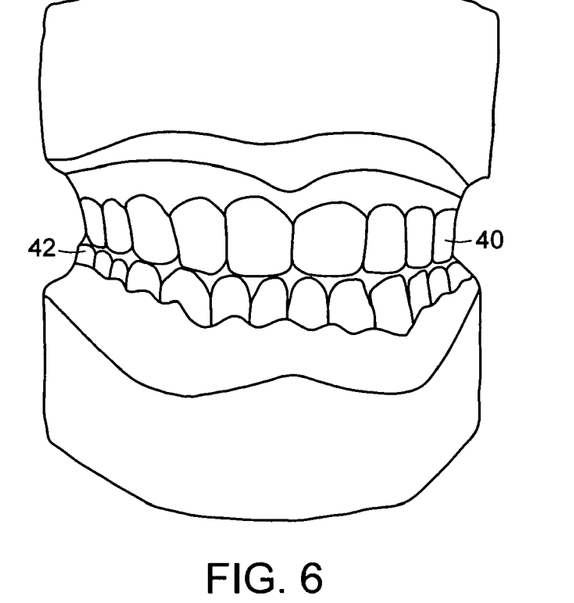
FIG. 6 is a front view of an upper set of teeth and a lower set of teeth during a representative bite of a patient.

FIG. 5 is a side view of the upper set of teeth 40 and the lower set of teeth 42 during a representative bite of a patient. FIG. 6 is a front view of the upper set of teeth 40 and the lower set of teeth 42 during a representative bite of a patient.

A cross bite is a deleterious force that puts the patient into a very susceptible position for a concussion. More specifically, the condyle 57 would not be in a concentric position in the glenoid fossa 61 and the condyle 57 of the mandible 50 is not in a best physiological position to withstand forces imparted to the jaw. In addition, the maxilla 68 and the mandible 50 are not positioned approximately parallel to one another.

Without the maxilla 68 and the mandible 50 positioned approximately parallel to one another, the patient having the upper set of teeth 40 and the lower set of teeth 42 is highly susceptible to experiencing a concussion when hit in the jaw. Equation 1 is an equation that governs the impact of a force delivered to the jaw. The force, F, that the patient receives is dictated by the mass of element making contact with the jaw, m, and the acceleration of the blow, a.

$$F=(m)a \qquad (1)$$

The force delivered to the jaw pushes the mandible 50 back and up to a point of least resistance in the jaw. As the mandible 50 is pushed back and upward, the condyle 57 of the mandible 50 pushes through an inferior joint space, pushes on the cartilage 55 and pushes up to a superior joint space. The condyle 57 transfers the force to the temporal bone 53 of the maxilla 68, where the temporal bone 53 radiates the force to the brain causing a concussion. Neither the condyle 57, the cartilage 55 or the temporal bone 53 can absorb the force, and instead transfer the force which is radiated to the brain.

Figure 7:
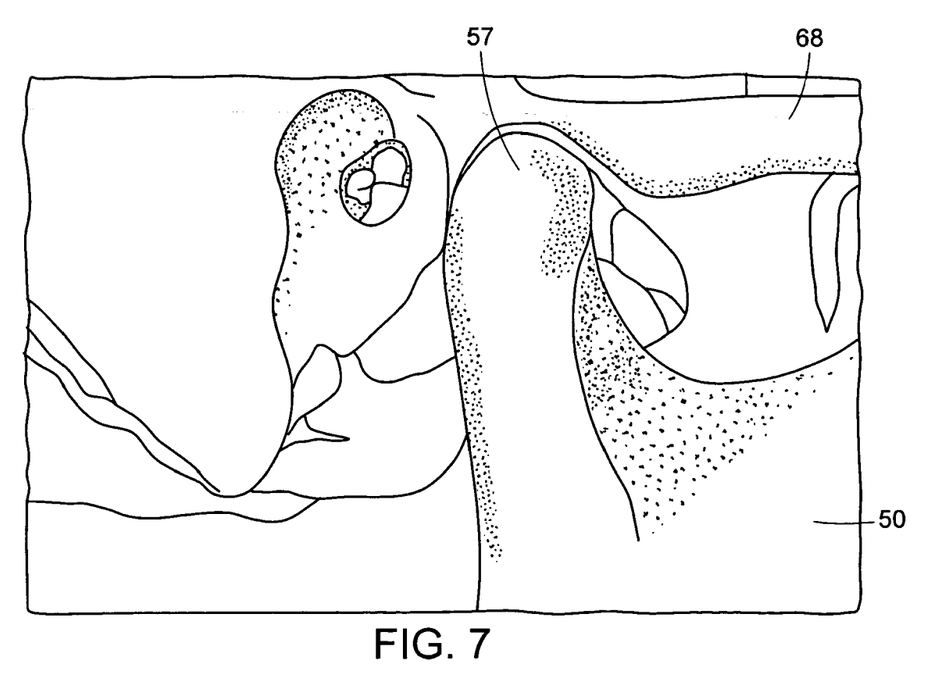
FIG. 7 shows a mandibular condyle in a closed packed position in the glenoid fossa.

FIG. 7 shows a mandibular condyle in a closed packed position in the glenoid fossa 61. FIG. 7 shows the mandible 50 overdosed with the maxilla 68 without the use of the dental appliance 75. As shown in FIG. 7, the condyle 57 of the mandible 50 contacts or comes close to the temporal bone 53 of the maxilla 68. The position shown in FIG. 7 is a deleterious position having a high probability of producing a concussion.

Figure 8:
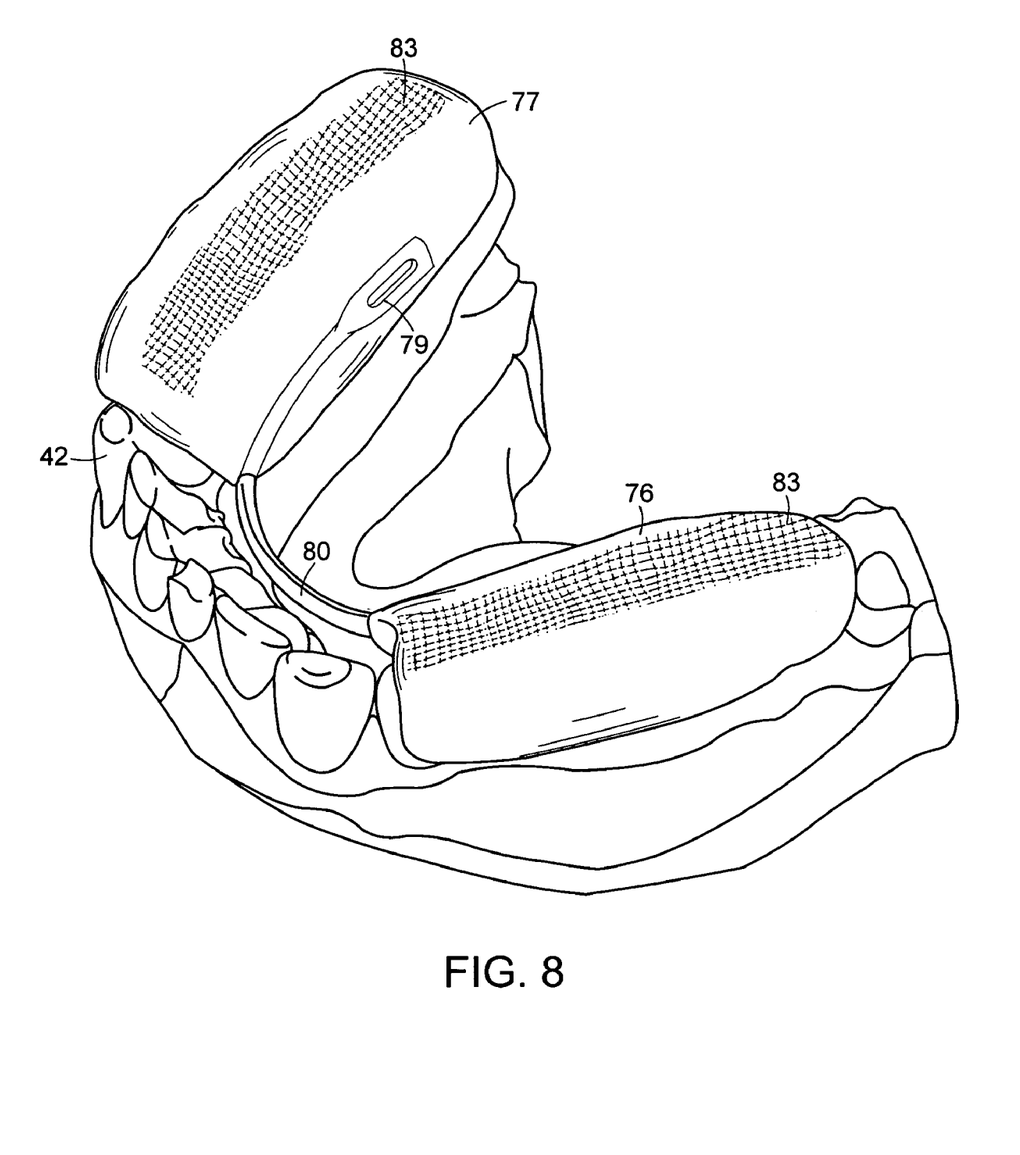
FIG. 8 is a view of a dental appliance covering at least a portion of an occlusion surface of several lower teeth of a patient.

FIG. 8 shows the dental appliance 75 covering at least a portion of the occlusion surface of several lower teeth 42. The dental appliance 75 is specifically molded to the teeth structure of the patient.

The acrylic on the left body 76 of the dental appliance 75 and the acrylic on the right body 77 of the dental appliance 75 fits over the second molars 18, 31, the first molars 19, 30, the second bicuspids 20, 29 and the first bicuspids 21, 28. In an embodiment, the acrylic on the left body 76 and the acrylic on the right body 77 fit over the first bicuspids 21, 28, the second bicuspids 20, 29 and the first molars 19, 30. In an embodiment, the dental appliance 75 comprises an acrylic that provides full coverage over the lower set of teeth 42. Full coverage from the acrylic over the lower set of teeth provides increased comfort to the patient and more stability between the maxilla 68 and the mandible 50 in instances such as when a patient is missing a tooth. Those skilled in the art will recognize the acrylic can cover any number of the lower set of teeth and be within the spirit and scope of the presently disclosed embodiments.

In an embodiment, the acrylic on the left body 76 of the dental appliance 75 and the acrylic on the right body 77 of the dental appliance 75 fits over the entire occlusion surface of several of the lower set of teeth 42 on the mandible 50. The diameter of the occlusion surface is dictated by the occlusion surface of the complementary upper set of teeth 40 of the maxilla 68. In an embodiment, the dental appliance 75 is wider on the bottom when the width of the teeth of the maxilla 68 are large. In an embodiment, the dental appliance 75 will be thinner on the bottom when the occlusion surface is small.

The left ball clasp 81 and the right ball clasp 82 in the acrylic of the dental appliance 75 are positioned slightly distal to the second bicuspid 20 on the left side 45 of the mandible 50 and the second bicuspid 29 on the right side 44 of the mandible 50. The ball clasps 81, 82 engage the teeth and maintain engagement between the teeth and the left body 76 and the right body 77. Those skilled in the art will recognize the left ball clasp and the right ball clasp can be positioned at various locations relative to the second bicuspids and be within the spirit and scope of the presently disclosed embodiments In an embodiment, the dental appliance 75 provides full occlusion of the cusps tips of the maxilla 68 to help lock the mandible 50 in place. In an embodiment, both the buckle and the lingual cusps of the upper set of teeth 40 of the maxilla 68 above the dental appliance 75 touch the dental appliance 75 on the mandible 50.

In an embodiment, there are indentations on the top on the left body 76 and the right body 77 to accept the cusps tips of the upper set of teeth 40 of the maxilla 68. The indentations on the top of the dental appliance 75 help keep the mandible 50 in place. The depth of the indentations for the acrylic varies from patient to patient and is based upon teeth geometry.

Figure 9:
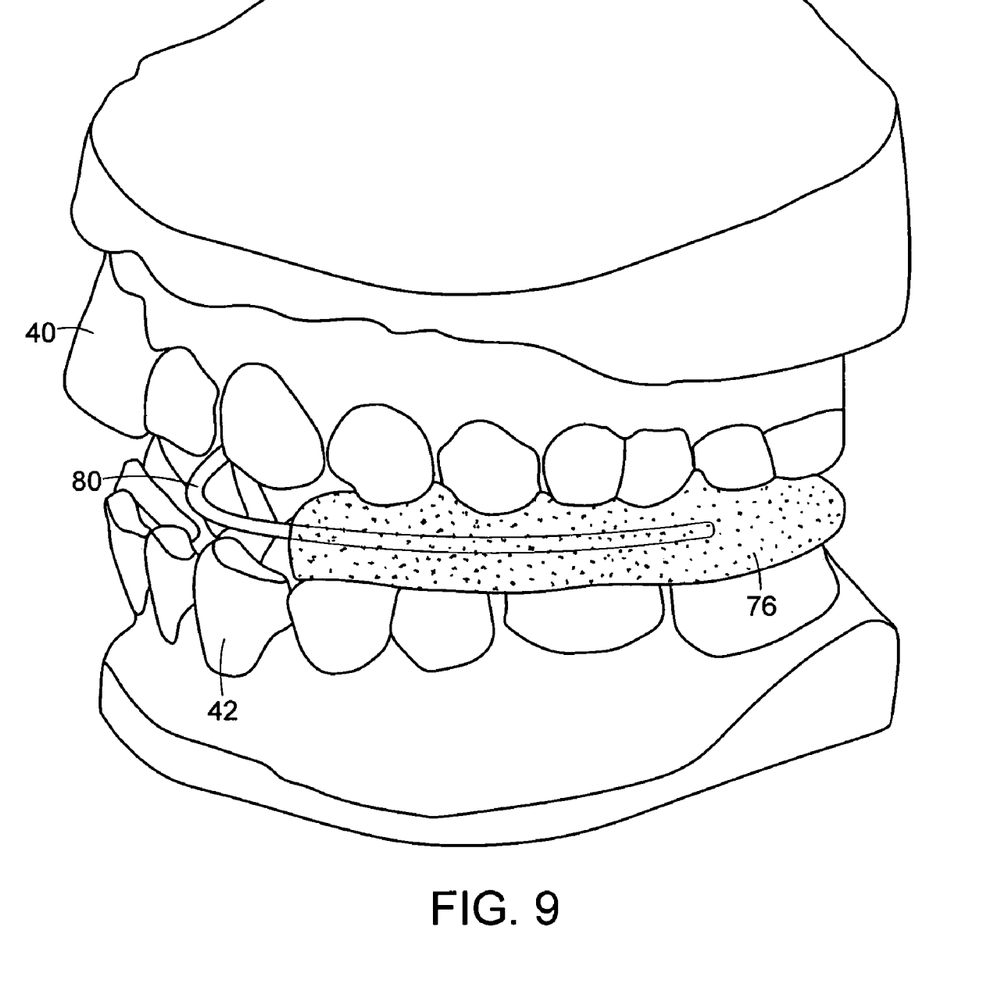
FIG. 9 is a model of an upper set of teeth and a lower set of teeth with a dental appliance covering at least a portion of an occlusion surface of several lower teeth of a patient during a representative bite of a patient.

FIG. 9 shows a model of the upper set of teeth 40 with the dental appliance 75 covering at least a portion of the occlusion surface of several lower teeth 42 of the mandible 50 during a representative bite of a patient.

The dental appliance 75 positions the condyle 57 equidistant both posterior and interior in the glenoid fossa 61 to balance the condyle 57 on both the left side and the right side of the jaw. The dental appliance 75 positions the mandible 50 and the maxilla 68 in an approximately parallel position with respect to one another and in doing so, positions the condyle 57 of the mandible 50 in the best physiological position to withstand forces imparted to the jaw.

Figure 10:
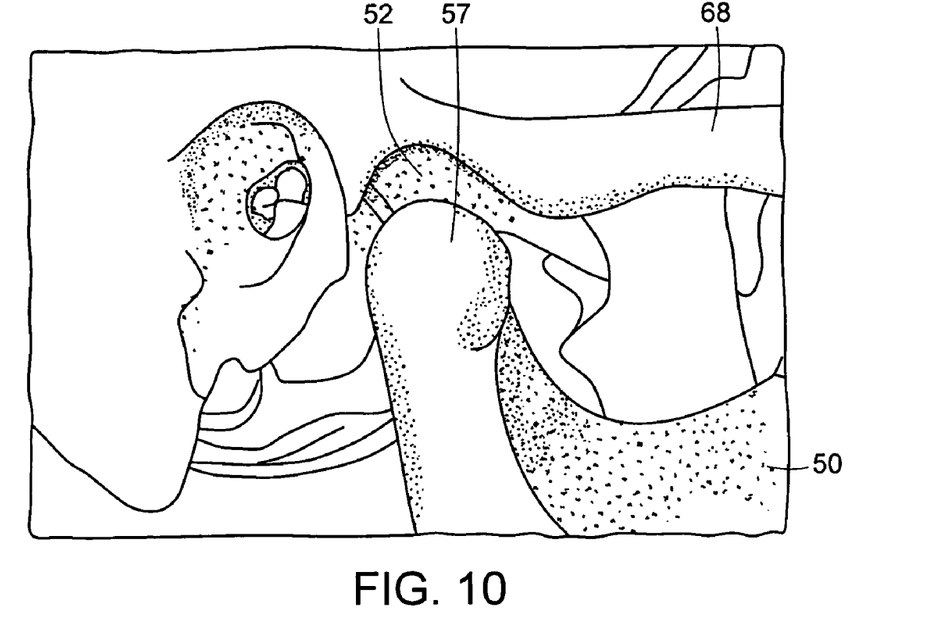
FIG. 10 shows the position of a condyle of a mandible relative to a maxilla with the use of the dental appliance.

FIG. 10 shows the position of the condyle 57 of the mandible 50 relative to the maxilla 68 with the use of the dental appliance 75. As shown in FIG. 10, the mandible 50 is separated from the maxilla 68.

The dental appliance 75 positions the condyle 57 downward, and approximately slightly forward and approximately in the center of the glenoid fossa 61. In an embodiment, the condyle 57 is positioned approximately one millimeter downward and slightly forward in the center of the glenoid fossa 61 and underneath the cartilage 55. Those skilled in the art will recognize the condyle 57 can be positioned various distances downward and slightly forward in the center of the glenoid fossa 61 and be within the spirit and scope of the presently disclosed embodiments.

The dental appliance 75 holds the condyle 57 in its concentric position in the glenoid fossa 61 and absorbs the force imparted to the jaw that would otherwise be transferred to the temporal bone 53. The dental appliance 75 serves as a force absorber to prevent the force transmitted from the condyle 57 to reach the temporal bone 53. The dental appliance 75 keeps the mandible 50 basically positioned and approximately stationary. The dental appliance 75 keeps the condyle 57 approximately stationary while preventing appreciable movement of the condyle 57 to keep it from getting closer to the brain via the temporal bone 53.

The dental appliance 75 is specifically designed to the geometry of the teeth of a patient and the type of bite the patient has. For example, in a patient with a class one occlusion with cross bites on the right side, the midline of the upper set of teeth 40 of the maxilla 68 line up with the midline of the lower set of teeth 42 of the mandible 50. The central incisors 8, 9 of the upper set of teeth 40 line up with the central incisors 24, 25 on the lower set of teeth 42 in order to place the condyle in a concentric position in the glenoid fossa. In an embodiment where the middle of the upper set of teeth 40 of the maxilla are not aligned with the midline of the lower set of teeth 42 of the mandible 50, the dental appliance 75 lines up the midline.

The thickness of the acrylic on portions of the left body 76 of the dental appliance 75 and the right body 77 of the dental appliance 75 is dictated when paralleling off the maxilla 68 and the mandible 50. The process of determining the thickness of the acrylic on portions of the left body 76 and the right body 77 begins with taking impressions of the maxilla 68 and the mandible 50. The condyle 57 is centered equidistant in the glenoid fossa 61 to make the maxilla 68 and the mandible 50 approximately parallel to one another when studying how the patient opens and closes their mouth. The thickness is determined using kinesiological principles, for example a deltoid strength test.

The deltoid strength test comprises determining a position of strength based upon a known thickness of spacers placed on the occlusion surface of one or more teeth. In an embodiment, the spacer is placed on the occlusion surface on the first molars 19, 30 of the mandible 50. The deltoid strength test is initially done in a position of strength whereby the mouth is open. In an embodiment, the level of strength is determined by a patient resisting an approximately vertical force applied to a patient's arm when the arms of the patient are extended in a horizontal direction. When the patient's mouth is open, the patient will be able to resist the applied force because this is a position of strength. Other kinesiological tests can be used including using the leg or other joints. Those skilled in the art will recognize there are other ways of measuring positions of strength that are within the spirit and scope of the presently disclosed embodiments.

The deltoid strength test is subsequently done in a position of weakness where the patient grits their teeth. In this position of weakness, there is very limited ability to resist the approximately vertical force applied to the hand since the temporomandibular joint 52 is in its end range of motion or its closed pack position. The bite is slowly opened up by placing spacers on the first molars 19, 30 to determine a position of strength using the deltoid strength test. The thickness of the acrylic on portions of the left body 76 of the dental appliance 75 and the right body 77 of the dental appliance 75 is determined from the thickness of spacers required to achieve the position of strength. For example, a thickness of the acrylic on portions of the left body 76 and the right body 77 ranging from about 2 millimeters to about 4 millimeters provide a position of strength. Those skilled in the art will recognize the thickness of the acrylic on portions of the left body 76 and the right body 77 can range from less than about 2 millimeters, between about 2 millimeters and about 4 millimeter and greater than about 4 millimeters and be within the spirit and scope of the presently disclosed embodiments.

The design of the dental appliance 75 is dependent upon the particular bite the patient has. For a collapsed bite occlusion where the lower set of teeth 42 of the mandible 50 are no longer in the plane of occlusion (i.e., submerged), the acrylic on portions of the left body 76 of the dental appliance 75 and the right body 77 of the dental appliance 75 is thicker to build up the acrylic more. For a super-eruption of the lower set of teeth 42 of the mandible 50, the acrylic is thinner. The dental appliance 75 eliminates the malocclusion of the teeth by ensuring the teeth do not hit in bad positions while lining up the midline of the upper set of teeth 40 of the maxilla 68 with the midline of the lower set of teeth 42 of the mandible 50.

Figure 11:
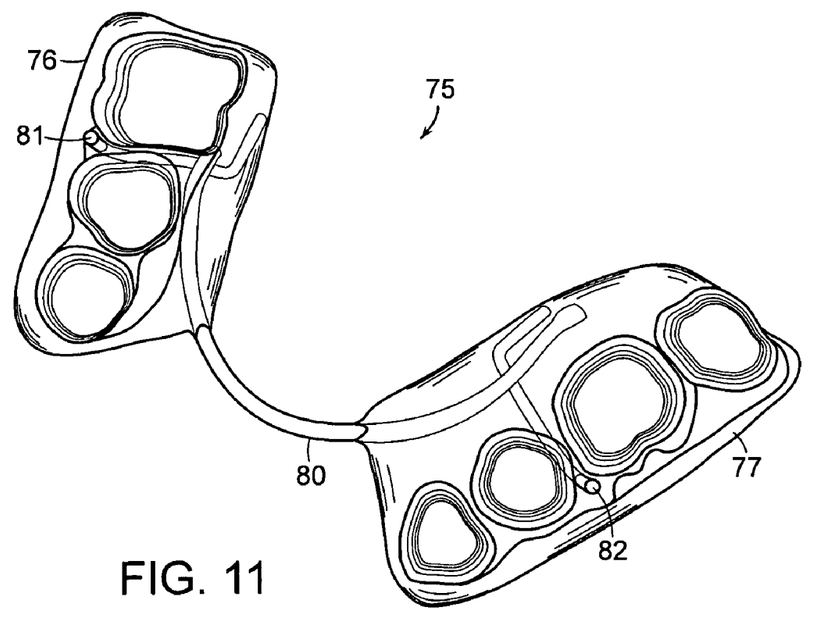
FIG. 11 shows an alternative embodiment of the dental appliance in which one body is shorter than the other body.

FIG. 11 shows an alternative embodiment of the dental appliance 75 in which the length of the acrylic of the left body 76 is shorter than the right body 77 due to extracted or damaged teeth of the patient. In FIG. 11, the a patient has a cracked second molar 18 and the length of the acrylic of the dental appliance 75 is shortened to not cover the decayed second molar. In this embodiment, the length of the acrylic on the left body 76 and the right body 77 is shorter than the embodiment shown in FIG. 1 and FIG. 2. As discussed above, the teeth coverage of the dental appliance 75 can vary from patient to patient as long as the dental appliance 75 positions the mandible 50 approximately parallel with the maxilla 68.

The dental appliance 75 provides benefits in addition to preventing concussions. The dental appliance 75 reduces stress while allowing for better concentration by putting the mandible 50 in a solid physiological position. With the dental appliance 75 in the mouth, the temporomandibular joint 52 is not in its end range motion or closed packed position while preventing the patient from clenching their teeth.

The dental appliance 75 is specially designed for phonetic purposes, allowing the patient to communicate well with the dental appliance placed on a portion of the lower set of teeth 42. In many instances, it is important for an athlete to be able to communicate with the dental appliance 75 placed on a portion of the lower set of teeth 42. In addition, the dental appliance 75 does not affect the ability of a person to drink liquids and does not retard breathing.

The presently disclosed embodiments are a method of preventing a head injury comprising: providing a dental appliance having a left body, a right body and a lingual bar engaging the left body and the right body; placing the dental appliance over a plurality of teeth of a lower jaw so the lower jaw and a upper jaw are approximately parallel; and absorbing a force applied to the lower jaw, wherein the dental appliance absorbs the force applied to the lower jaw while preventing a condyle of a mandible from transferring the force to a temporal bone.

The presently disclosed embodiments are a method of preventing a concussion comprising: providing a dental appliance having a left body, a right body and a lingual bar engaging the left body and the right body; and placing the dental appliance over a portion of a lower set of teeth; wherein the dental appliance positions a maxilla and a mandible in an approximately parallel position to absorb a force applied to a jaw.

The presently disclosed embodiments are a method of manufacturing a dental appliance to prevent head injury comprising: making a model of the teeth of the upper jaw and the lower jaw; forming a left body to fit over a plurality of teeth of the left lower jaw; forming a right body to fit over a plurality of teeth of the right lower jaw; and engaging a lingual bar to the left body and the right body, the lingual bar having a shape following a contour of the teeth of the lower jaw, wherein the dental appliance covers a plurality of teeth of the lower jaw to place a mandible and a maxilla in an approximately parallel alignment.

The dental appliance 75 can be manufactured using the following process. First, an impression of the patient's mouth is taken to create a mold of the mouth. A model of the upper and lower jaws is created from the mold. The model is surveyed, and undercuts not needed for retention are blocked out. The model can then be duplicated. The model can be articulated using wax repositioning bite or any other bite material.

Next, evaluate arch for proper length lingual bar and lingual bend bar into position leaving sufficient relief. Mark and score lingual bar at mesial of first bicuspid for finish line. Roughen posterior segments of bar for increased retention. Lute bar into position, with sticky wax, at lingual of model.

Next, bend ball clasps interproximally between bicuspids or second bicuspid and first molar as indicated. Bring over occlusion of teeth and bend "tail" along lingual bar. Lute ball clasps to bar with self-cure clear acrylic to prevent movement.

For strength and accuracy, the preferred method is injection using clear hard material although clear hard press pack method can be used. The following steps apply when investing for heat cure.

Apply wax onto lingual of model from molars through first bicuspid finish line, covering bar and lingual of teeth. Wax occlusion of teeth extending over buccal for added retention. Occlude with opposing model. Trim wax and check for proper contact.

Next, invest model in lower half of denture flask with plaster, covering exposed lingual bar, leaving only wax exposed. Apply separator to smoothed surface of plaster investment. Invest top half of flask. When fully set, boil out wax and apply tin foil substitute to all surfaces. When dry, apply second coat of separator and allow to dry.

Next, mix clear hard acrylic and inject following methods known in the art. Cure and then cool processed appliance. Break out of flask.

Next, finish using methods known in the art. Trial fit on master model and check occlusion. Polish completed dental appliance.

Those skilled in the art will recognize that steps may be added or removed from the above description or the order of the steps may be varied and still be within the spirit and scope of the presently disclosed embodiments.

All patents, patent applications, and published references cited herein are hereby incorporated by reference in their entirety. It will be appreciated that various of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. A method of preventing a head injury in a person comprising:

providing a dental appliance having a left body, a right body and a non-adjustable rigid lingual bar, wherein a portion of the rigid lingual bar is embedded within a material comprising the left body and a portion of the rigid lingual bar is embedded within a material comprising the right body, wherein the left body, the right body and the non-adjustable rigid lingual bar are each sized, shaped and dimensioned for the person, wherein the dental appliance is custom manufactured for the person based on a model of teeth of an upper jaw and a lower jaw of the person taken when an articular disc of a temporomandibular joint of the person is superior to a condyle of the temporomandibular joint to position the upper jaw approximately parallel to the lower jaw;

placing the dental appliance in a mouth of the person over a plurality of teeth of the lower jaw, wherein the person has an unparallel jaw alignment, wherein placement of the dental appliance over the lower jaw positions the articular disc of the temporomandibular joint superior to the condyle of the temporomandibular joint, and places the lower jaw approximately parallel to the upper jaw, wherein the rigid lingual bar follows a contour on a posterior surface of a lower set of teeth of the lower jaw; and absorbing a force applied to the lower jaw, wherein the dental appliance absorbs the force applied to the lower jaw while preventing the condyle from transferring the force to a temporal bone.

2. The method of claim 1 wherein placement of the dental appliance over the lower jaw positions the condyle in a position downward and slightly forward and approximately in a center of a glenoid fossa.

3. The method of claim 1 further comprising wherein placement of the dental appliance over the lower jaw lines up a midline of the mouth.

4. The method of claim 1 further comprising wherein placement of the dental appliance over the lower jaw positions the condyle approximately equidistant from both posterior and interior in a glenoid fossa.

5. The method of claim 1 wherein placement of the dental appliance over the lower jaw holds the condyle in a concentric position in a glenoid fossa.

6. A method of preventing a concussion in a person comprising:

providing a dental appliance having a left body, a right body and a non-adjustable rigid lingual bar, wherein a portion of the rigid lingual bar is embedded within a material comprising the left body and a portion of the rigid lingual bar is embedded within a material comprising the right body, wherein the left body, the right body and the non-adjustable rigid lingual bar are each sized, shaped and dimensioned for the person, and wherein the dental appliance is custom manufactured for the person based on a model of teeth of an upper jaw and a lower jaw of the person taken when an articular disc of a temporomandibular joint of the person is superior to a condyle of the temporomandibular joint to position the upper jaw approximately parallel to the lower jaw; and placing the dental appliance in a mouth of the person over a portion of a lower set of teeth, wherein the person has an unparallel jaw alignment, wherein placement of the dental appliance over the lower set of teeth positions the articular disc of the temporomandibular joint of the person superior to the condyle of the temporomandibular joint, wherein the rigid lingual bar follows a contour on a posterior surface of the lower set of teeth;

wherein the dental appliance positions the upper jaw and the lower jaw in an approximately parallel position to absorb a force applied to a jaw.

7. The method of claim 6 wherein the dental appliance prevents the condyle of the lower jaw from transferring the force to a temporal bone.

8. The method of claim 6 wherein placement of the dental appliance over the lower set of teeth places the condyle of the lower jaw in a physiological position to withstand the force.

9. The method of claim 6 wherein placement of the dental appliance over the lower set of teeth positions the condyle underneath a cartilage in the jaw.

10. The method of claim 6 wherein placement of the dental appliance over the lower set of teeth positions the condyle in a position downward and slightly forward and approximately in a center of a glenoid fossa.

11. The method of claim 6 wherein placement of the dental appliance over the lower jaw lines up a midline of the mouth.

12. The method of claim 6 wherein placement of the dental appliance over the lower set of teeth positions the condyle approximately equidistant from both posterior and interior in a glenoid fossa.

13. The method of claim 6 wherein placement of the dental appliance over the lower set of teeth holds the condyle in a concentric position in a glenoid fossa.

14. A method of manufacturing a dental appliance to prevent head injury in a person comprising:

making a model of teeth of an upper jaw and a lower jaw of a mouth of the person having an unparallel jaw alignment, wherein the model is taken when an articular disc of a temporomandibular joint of the person is superior to a condyle of the temporomandibular joint to position the upper jaw approximately parallel to the lower jaw;

forming a left body to fit over a plurality of teeth of a left side of the lower jaw, wherein the left body is sized, shaped and dimensioned to fit over the plurality of teeth;

forming a right body to fit over a plurality of teeth of a right side of the lower jaw, wherein the right body is sized, shaped and dimensioned to fit over the plurality of teeth; and embedding at least a portion of a non-adjustable lingual bar into the left body and into the right body, the lingual bar sized, shaped and dimensioned to follow a contour on a posterior surface of a lower set of teeth of the lower jaw wherein the dental appliance covers a plurality of teeth of the lower jaw to place a mandible and a maxilla in an approximately parallel alignment.

15. A dental appliance for preventing head injury in a person having an unparallel jaw alignment comprising:

a left body sized, shaped and dimensioned for the person;

a right body sized, shaped and dimensioned for the person; and a non-adjustable rigid lingual bar sized, shaped and dimensioned for the person, wherein the rigid lingual bar spans from the left body to the right body to engage the left body to the right body, wherein a portion of the rigid lingual bar is embedded within a material comprising the left body and a portion of the rigid lingual bar is embedded within a material comprising the right body, wherein the dental appliance is custom manufactured for the person based on a model of teeth of an upper jaw and a lower jaw of the person taken when an articular disc of a temporomandibular joint of the person is superior to a condyle of the temporomandibular joint to position the upper jaw approximately parallel to the lower jaw, and wherein the dental appliance covers a portion of a lower set of teeth while positioning the articular disc of the temporomandibular joint superior to the condyle of the temporomandibular joint and while placing the upper jaw approximately parallel to the lower jaw.

16. The dental appliance of claim 15 further comprising a left ball clasp extending through at least a portion of the left body and a right ball clasp extending through at least a portion of the right body.

17. The dental appliance of claim 15 further comprising a mesh material within the left body and the right body.

18. The dental appliance of claim 15 further comprising indentations on a top portion of the left body and a top portion of the right body for the cusps tips of an upper set of teeth above the left body and the right body.

19. The dental appliance of claim 15 wherein the rigid lingual bar is shaped to follow a contour on a posterior surface of the lower set of teeth.

20. The dental appliance of claim 15 wherein the dental appliance places the condyle of the upper jaw in a physiological position to absorb a force applied to a jaw.

* * * * *

UNITED STATES PATENT AND TRADEMARK OFFICE
CERTIFICATE OF CORRECTION

PATENT NO. : 7,827,991 B2
APPLICATION NO. : 11/181589
DATED : November 9, 2010
INVENTOR(S) : Gerald J. Maher

It is certified that error appears in the above-identified patent and that said Letters Patent is hereby corrected as shown below:

Col. 11, Ln. 8, Delete "further comprising"

Col. 11, Ln. 11, Delete "further comprising"

Signed and Sealed this

Twenty-first Day of December, 2010

David J. Kappos
*Director of the United States Patent and Trademark Office*